United States Patent
Tian et al.

(10) Patent No.: US 8,064,723 B2
(45) Date of Patent: Nov. 22, 2011

(54) METHOD AND APPARATUS FOR FAST VOLUME RENDERING OF 3D ULTRASOUND IMAGE

(75) Inventors: Yong Tian, Shenzhen (CN); Bin Yao, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1065 days.

(21) Appl. No.: 11/876,639

(22) Filed: Oct. 22, 2007

(65) Prior Publication Data

US 2008/0262353 A1    Oct. 23, 2008

(30) Foreign Application Priority Data

Apr. 19, 2007 (CN) .......................... 2007 1 0102736

(51) Int. Cl.
*G06K 9/00* (2006.01)
*G06K 9/40* (2006.01)

(52) U.S. Cl. ........ 382/276; 382/278; 382/282; 382/285; 382/299; 382/308

(58) Field of Classification Search .......... 382/173–175, 382/181–182, 202, 203, 205, 225, 276, 278, 382/282, 285, 299, 308
See application file for complete search history.

(56) References Cited

U.S. PATENT DOCUMENTS

| | | | |
|---|---|---|---|
| 6,155,978 A | 12/2000 | Cline et al. | |
| 6,289,135 B1 * | 9/2001 | Declerck et al. | 382/276 |
| 6,512,993 B2 * | 1/2003 | Kacyra et al. | 702/159 |
| 6,858,826 B2 * | 2/2005 | Mueller et al. | 250/208.1 |
| 7,043,290 B2 * | 5/2006 | Young et al. | 600/416 |
| 7,098,435 B2 * | 8/2006 | Mueller et al. | 250/208.1 |
| 7,271,377 B2 * | 9/2007 | Mueller et al. | 250/208.1 |
| 7,272,265 B2 * | 9/2007 | Kouri et al. | 382/260 |
| 7,657,299 B2 * | 2/2010 | Huizenga et al. | 600/410 |
| 7,778,493 B2 * | 8/2010 | Ho et al. | 382/299 |
| 7,920,440 B2 * | 4/2011 | Jiang et al. | 367/11 |
| 8,014,625 B2 * | 9/2011 | Dewaele | 382/267 |
| 2004/0071363 A1 * | 4/2004 | Kouri et al. | 382/276 |
| 2004/0181151 A1 | 9/2004 | Sumanaweera et al. | |
| 2005/0187474 A1 | 8/2005 | Kwon | |
| 2005/0240104 A1 | 10/2005 | Shim et al. | |
| 2005/0283075 A1 | 12/2005 | Ma et al. | |
| 2006/0020207 A1 | 1/2006 | Pagoulatos et al. | |

FOREIGN PATENT DOCUMENTS

| | | |
|---|---|---|
| CN | 1457474 | 11/2003 |
| CN | 1963869 | 5/2007 |
| CN | 1967595 | 5/2007 |
| JP | 2005006718 | 1/2005 |
| JP | 2005328957 | 12/2005 |

* cited by examiner

*Primary Examiner* — David A Vanore
(74) *Attorney, Agent, or Firm* — Kory D. Christensen; Stoel Rives LLP (57) ABSTRACT

The invention provides a method and apparatus for fast volume rendering of 3D ultrasound image, comprising a dividing step, a calculating step, a determining step, a morphological closing operation step and a filling step, wherein each flat grid can be entirely filled by obtaining gray-scale values for all pixels inside the grid through interpolating; for the non-flat grid, the steps of dividing, calculating, determining and filling are performed repeatedly until the non-flat grid is subdivided into atomic grids to calculate gray-scale values for remaining pixels by projection. As the method can be finished in the rear end, no difficulty occurs in the implementation, and no process for being adapted to previous frames is required. Therefore, the method can improve the rendering speed effectively without degrading the quality of image to put 3D ultrasound imaging to the best use.

22 Claims, 8 Drawing Sheets

(prior art)

Fig.13

METHOD AND APPARATUS FOR FAST VOLUME RENDERING OF 3D ULTRASOUND IMAGE

STATEMENT OF RELATED APPLICATION

The present application claims priority of the Chinese Patent Application No. 200710102736, entitled "Method and Apparatus for Fast Volume Rendering of 3D Ultrasound Image", filed on Apr. 19, 2007, which is incorporated herein by reference in its entirety.

FIELD OF THE INVENTION

The present invention relates to a method and an apparatus for rendering an image, in particular to a method and an apparatus for fast volume rendering of 3D ultrasound image.

BACKGROUND OF THE INVENTION

As traditional medical imaging equipment can only offer two-dimensional (hereinafter referred to as 2D) image of a human body inside, a doctor can just estimate the size and the shape of pathology from a plurality of 2D images so as to "conceive" the three-dimensional (hereinafter referred to as 3D) geometrical relationship between the pathology and its surrounding tissue, which brings difficulty in therapy. However, 3D visualization technology can reconstruct a 3D image from a series of 2D images and display it on a terminal. Therefore, not only a visual integral concept on the imaged object can be obtained, but also a lot of important 3D information can be saved. As the ultrasound imaging has significant advantages over CT, MRI in non-invasion, non-ionizing radiation and operation flexibility etc., the 3D ultrasound imaging certainly will be used widely in medical clinic. Therefore, it is indispensable to research 3D visualization technology of the ultrasound field.

Recently, there are two ways to acquire 3D ultrasound volume data: one is to acquire a series of 2D ultrasound images for tissues at known spatial positions using available 2D ultrasound diagnostic equipment in combination with a certain locating machine so as to obtain 3D volume data in an offline manner; the other is to acquire 3D volume data in real time using a 2D matrix array probe to emit volume ultrasound beams in pyramid shape.

"Rendering" means to obtain visual information using a visual algorithm to calculate volume data and finally display the visual information on a computer screen. Currently, 3D visual algorithms for ultrasound images are mainly divided into two classes. One is Surface Rendering, in which volume data should be classified to form intermediate geometrical elements, and then image rendering is achieved by means of traditional computer graphics technology. However, this algorithm is easily apt to produce a false plane display and cavity phenomenon for ultrasound images. The other is Direct Volume Rendering, in which 2D images displayed on the screen are generated directly from volume data. Using this algorithm, need for classifying the volume data and forming intermediate geometrical elements is eliminated, 3D medicinal information in detail is maintained and effects of integrative rendering are enhanced. However, this algorithm also increases the overhead for computation.

Figure 1:
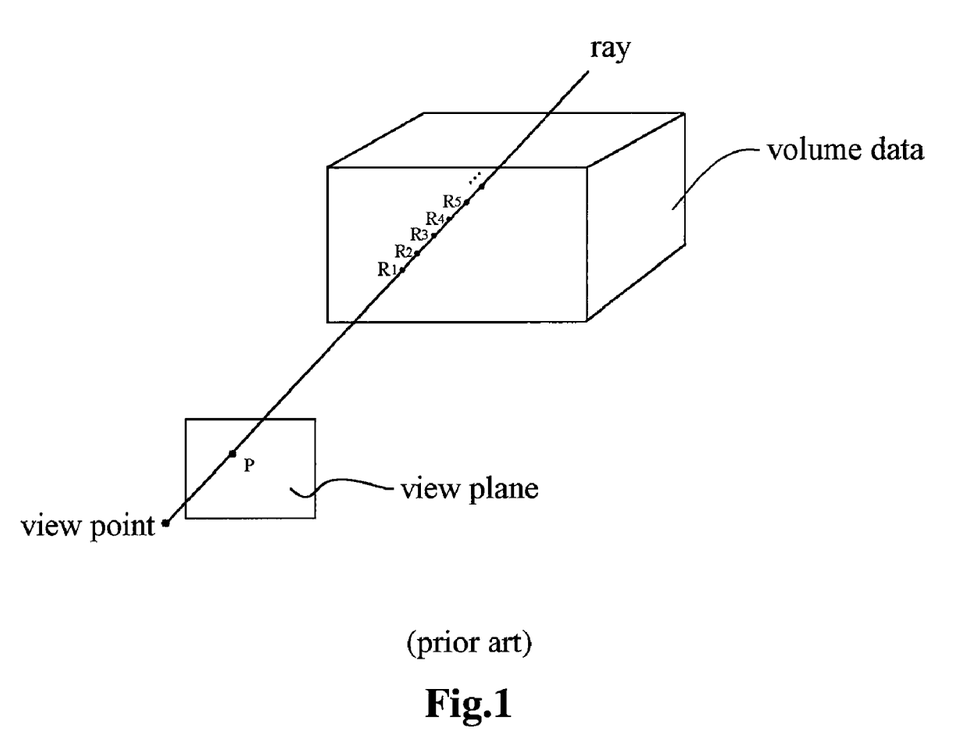
FIG. 1 is a schematic diagram illustrating a ray casting algorithm.

Ray casting algorithm is a method for direct volume rendering with principles as follows: virtual rays are emitted in the direction of connection between view point and each pixel on the view plane image and passes through and re-samples the volume data; and then gray-scale value of the pixel is finally obtained by synthesizing the re-sampled volume data according to an optical absorption-emission model, as shown in FIG. 1. This algorithm is a classical method for visualizing 3D volume data, but for a large amount of volume data of 3D ultrasound image, it is difficult to meet real-time demand because of high overhead for computation.

In fact, to be real-time is a vital factor that has restricted the practical application of 3D ultrasound for years. Therefore, researches on methods for fast rendering of 3D ultrasound images become essential and will be significant for medical clinic.

A method for accelerating 3D ultrasound imaging is disclosed in a patent document US 2002/0007680 A1, entitled "Method for Examining Objects using Ultrasound". In this document, the method is described as follows: dividing volume data into several regions and determining whether or not more information is included in the part of the object corresponding to each region; applying higher scanning density and/or faster scanning frequency to the part of the object with more information, otherwise, applying sparser scanning density and/or slower scanning frequency. However, the method disclosed in the above-mentioned patent document is performed in the front end and it is difficult to manufacture such equipment. Besides, The method suffers from two main disadvantages. The first disadvantage lies in the rough division of the volume data, thereby it is hard to ensure the consistency of information density in each part of one region. The second disadvantage derives from inaccuracy of using "a moving detector" to determine whether or not the part of the object corresponding to each region has more information. Following are the reasons. Firstly, intensity of movement cannot completely represent density of information. Secondly, the result determined from current frame data will not guarantee to be effective in next frame. Thirdly, each time when the equipment is initiated and parameters are changed, rendering can be stable only after at least being adapted to the first two frames.

SUMMARY OF THE INVENTION

The objective of the present invention is to overcome the disadvantages of present methods, and provide a method and an apparatus for volume rendering of 3D ultrasound image to realize fast and accurate rendering of 3D ultrasound image. In order to achieve this objective, the technical solution adopted in the present invention is as follows:

According to the first aspect of the embodiment of the present invention, there is provided a method for fast volume rendering of 3D ultrasound image, comprising the steps of: dividing a view plane into first-level grids arranged vertically and horizontally according to a predetermined size; calculating gray-scale values of pixels on four vertices of each grid by projection; comparing deviations among the gray-scale values of pixels on four vertices of each grid with a predetermined threshold, wherein if the deviation is smaller than the predetermined threshold, the grid is determined as a flat grid, and if the deviation is larger than the predetermined threshold, the grid is determined as a non-flat grid; and filling each flat grid by obtaining gray-scale values for all pixels inside the grid through interpolating the gray-scale values of pixels on four vertices thereof; wherein for the non-flat grids, repeating the steps of dividing, calculating, determining and filling until the non-flat grids are subdivided into atomic grids so as to calculate gray-scale values for remaining pixels by projection.

Optionally, the method for fast volume rendering of 3D ultrasound image according to the embodiment of the present invention further comprises a morphological closing operation step for performing a morphological closing operation on a set of non-flat grids in this level each time when finishing the determining step; and wherein the non-flat grids generated in the closing operation which occur in the flat grids in this level are retained and which occur in low-level flat grids are discarded.

Preferably, in the dividing step, adjacent grids can be divided to share vertices or boundaries, and thus, in the calculating step, it is only to calculate the gray-scale values of pixels on non-sharing grids and retrieve the calculated and saved results with regard to the gray-scale values of pixels on grids which share the vertices or boundaries.

Yet preferably, in the dividing step, the view plane is divided into first-level grids arranged vertically and horizontally according to a predetermined size that the width is equal to the height, in which the width of the first-level grids is equal to the height and both are the integer power of 2, expressed as:

$$W_1 = H_1 = 2^{\lfloor log_2 min(\frac{X}{x}, \frac{Y}{y}) \rfloor},$$

wherein $W_1$ and $H_1$ are respectively the width and the height of the first-level grid, X and Y are respectively the width and the height of the view plane, and x and y are respectively expected numbers of columns and rows of the first-level grids.

Further preferably, the non-flat grid is subdivided repeatedly in the dividing step into four even sub-grids shaped as "田"(i.e. a 2×2 array).

Further preferably, in the determining step, the deviation between gray-scale values of pixels on two diagonal vertices of each grid is compared with a predetermined threshold, which is expressed as follows:

$$\begin{cases} |I_{An} - I_{Dn}| < T \\ |I_{Bn} - I_{Cn}| < T \end{cases},$$

in which the formula for calculating the threshold T is:

$$T = \frac{\delta}{W_n} \cdot \frac{I_{An} + I_{Bn} + I_{Cn} + I_{Dn}}{4} = \frac{\delta \cdot 2^{n-3} \cdot (I_{An} + I_{Bn} + I_{Cn} + I_{Dn})}{W_1},$$

wherein n is the level of the current grid, $I_{An}, I_{Bn}, I_{Cn}, I_{Dn}$ are the gray-scale values for four vertices of the current grid respectively, $W_n$ and $W_1$ are the width of n-level and first-level grids respectively, and a coefficient δ is a constant which can be equal to 2 upon experience.

Alternatively, in the determining step, the variance of the gray-scale values of pixels on four vertices of each grid is compared with a predetermined threshold to determine whether or not the grid is a flat or a non-flat grid.

In the filling step, the gray-scale values for all pixels inside each grid can be obtained through a bilinear or a non-linear interpolation using the gray-scale values of pixels on four vertices of each grid.

Additionally, in the dividing step, dividing can be set to stop at a certain level. Then, all pixels in the non-flat grid can be calculated using a ray casting algorithm.

According to the second aspect of the embodiment of the present invention, there is provided an apparatus for fast volume rendering of 3D ultrasound image, comprising: a dividing module for dividing a view plane into first-level grids arranged vertically and horizontally according to a predetermined size; a calculating module for calculating gray-scale values of pixels on four vertices of each grid by projection; a determining module for comparing deviations among the gray-scale value of pixels on four vertices of each grid with a predetermined threshold, wherein if the deviation is smaller than the predetermined threshold, the grid is a flat grid, and if the deviation is larger than the predetermined threshold, the grid is a non-flat grid; and a filling module for filling each flat grid by obtaining gray-scale values for all pixels inside the grid through interpolating the gray-scale values of pixels on four vertices thereof; wherein the non-flat grids are repeatedly processed by the dividing module, the calculating module, the determining module and the filling module till the non-flat grids are subdivided into atomic grids so as to calculate gray-scale values for remaining pixels by projection.

Optionally, the apparatus for fast volume rendering of 3D ultrasound image according to the embodiment of the present invention further comprises a morphological closing operation module for performing a morphological closing operation on a set of non-flat grids of this level each time when the determining module executes the determining; and wherein the non-flat grids generated in the closing operation which occur in the flat grids in this level are retained and which occur in low-level flat grids are discarded.

Preferably, the dividing module can divide the adjacent grids to share vertices or boundaries, and thus the calculation module only calculates gray-scale values of pixels on non-shared grids, and retrieves the calculated and saved result with regard to the gray-scale values of pixels on grids which share the vertices or boundaries.

Yet preferably, the dividing module divides the view plane into first-level grids arranged vertically and horizontally according to a predetermined size that the width is equal to the height, in which the width of the first-level grids is equal to the height and both are the integer power of 2, expressed as:

$$W_1 = H_1 = 2^{\lfloor log_2 min(\frac{X}{x}, \frac{Y}{y}) \rfloor},$$

wherein $W_1$ and $H_1$ are respectively the width and the height of the first-level grids, X and Y are respectively the width and the height of the view plane, and x and y are respectively expected numbers of columns and rows of the first-level grids.

Further preferably, the non-flat grid is subdivided repeatedly by the dividing module into four even sub-grids shaped as "田"(i.e. a 2×2 array).

Further preferably, the determining module compares the deviation between gray-scale values of pixels on two diagonal vertices of each grid with a predetermined threshold, which is expressed as follows:

$$\begin{cases} |I_{An} - I_{Dn}| < T \\ |I_{Bn} - I_{Cn}| < T \end{cases},$$

in which the formula for calculating the threshold T is:

$$T = \frac{\delta}{W_n} \cdot \frac{I_{An} + I_{Bn} + I_{Cn} + I_{Dn}}{4} = \frac{\delta \cdot 2^{n-3} \cdot (I_{An} + I_{Bn} + I_{Cn} + I_{Dn})}{W_1},\qquad(5)$$

wherein n is the level of the current grid, $I_{An}$, $I_{Bn}$, $I_{Cn}$, $I_{Dn}$ are respectively the gray-scale values for four vertices of the current grid, $W_n$ and $W_1$ are respectively the width of n-level and first-level the grids, and a coefficient δ is a constant which is equal to 2 upon experience.

Alternatively, the determining module determines whether or not the grid is a flat or a non-flat grid by comparing the variance of the gray-scale values of pixels on four vertices of each grid with a predetermined threshold.

The filling module can obtain the gray-scale values for all pixels inside each grid through a bilinear or a non-linear interpolation using the gray-scale values of pixels on four vertices of each grid.

Additionally, the dividing module can be set to stop at a certain level. Then, all pixels in the non-flat grid can be calculated using a ray casting algorithm.

Since the method according to the embodiment of the present invention is finished in rear end, no difficulty occurs in the implementation. Besides, need for being adapted to previous frames is eliminated as both the precision and accuracy of division excel that of the prior art. Therefore, the method according to the embodiment of the present invention can improve the rendering speed more effectively without degrading the quality of image to make full play of the advantages of 3D ultrasound imaging.

DETAILED DESCRIPTION OF THE INVENTION

Figure 2:
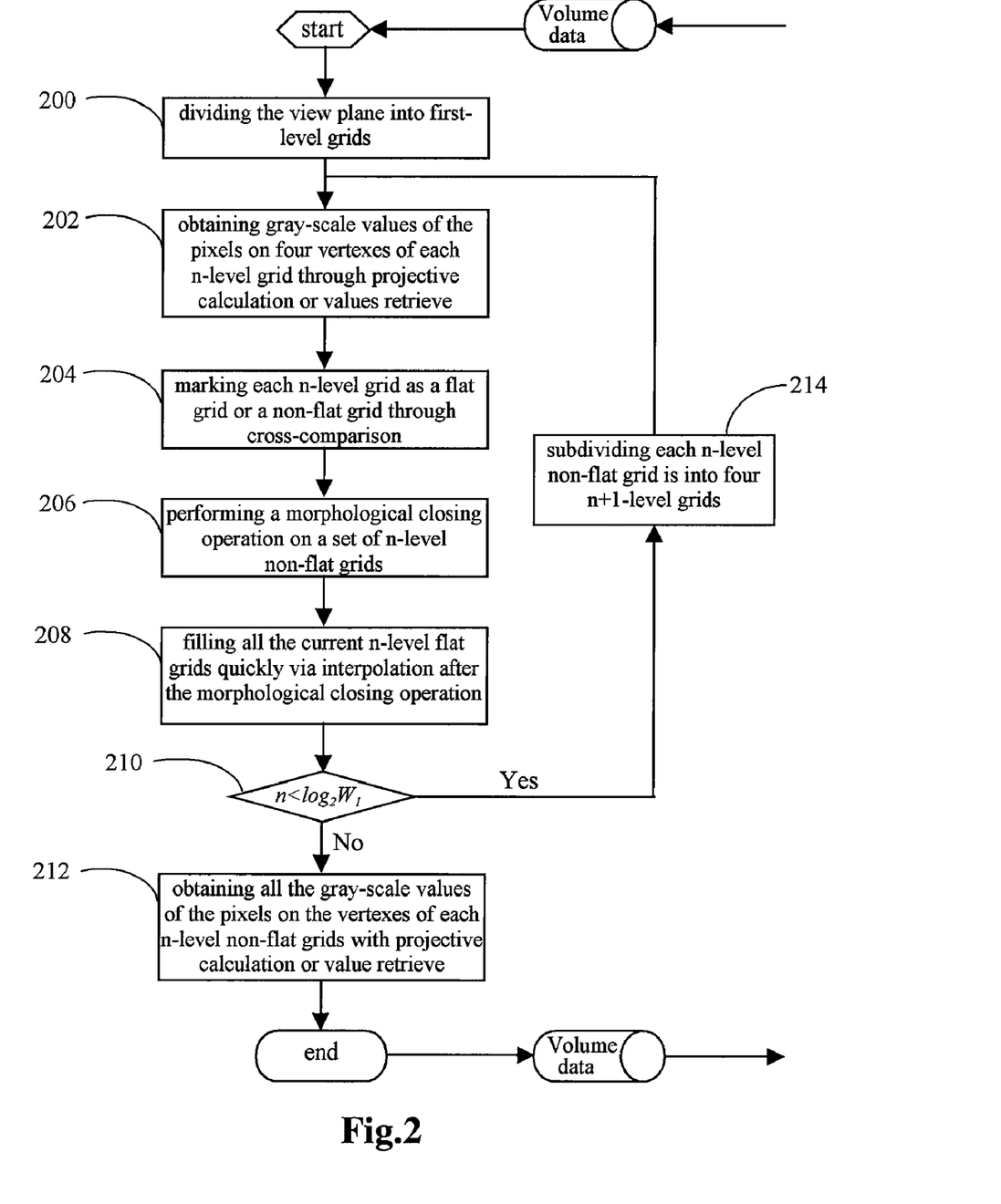
FIG. 2 is a flow chart of a method for fast volume rendering of 3D ultrasound image according to the embodiment of the present invention.

FIG. 2 is a flow chart of the method for fast volume rendering of 3D ultrasound image according to the embodiment of the present invention. Said method comprises following steps: As to 3D volume data, dividing the view plane into first-level grids (step 200), and then obtaining gray-scale values of the pixels on four vertices of each n-level grid through projective calculation or values retrieve (step 202); marking each n-level grid as a flat grid or a non-flat grid through cross-comparison (step 204); performing a morphological closing operation on a set of n-level non-flat grids (step 206), and filling all the current n-level flat grids quickly via interpolation after the morphological closing operation (step 208); determining (step 210) the "level" n of the divided grid ("level" herein referred to as hierarchy of the divided grid), wherein if the level n≧$\log_2 W_1$, all gray-scale values of pixels on the vertices of each n-level non-flat grids are obtained with projective calculation or value retrieve (step 212), and if the level number n<$\log_2 W_1$, each n-level non-flat grid is subdivided into four n+1-level grids (step 214), and then back to step 202 to recalculate the gray-scale values of pixels on the vertices of the grid and going on with subsequent processing. Each step in this method of the embodiment of the present invention will be detailed below.

First of all, the whole view plane is divided regularly into grids arranged vertically and horizontally, which are known as "first-level grids". Here, it is required to determine the size of the first-level grid, which should be substantially proportional to the size of the view plane upon experience. Moreover, for the purpose of convenient calculation, the width is generally equal to the height and both are the integer power of 2. The formula adopted is as follows:

$$W_1 = H_1 = 2^{\lfloor \log_2 \min\left(\frac{X}{x}, \frac{Y}{y}\right) \rfloor},\qquad(1)$$

wherein $W_1$ and $H_1$ are respectively the width and the height of the first-level grid, X and Y are respectively the width and the height of the view plane (units of $W_1$, $H_1$, X and Y are all pixels), and x and y are respectively expected numbers of columns and rows of the first-level grids. Since the grid is always a square, $W_1$ is also known as "first-level side length". In practice, typical parameters are X=640, Y=480, x=80, y=60, $W_1$=8.

In the process of dividing the first-level grids, a portion with the width of X % $W_1$ and the height of Y % $W_1$ at edge of the view plane will be discarded if X or Y can not be exactly divided by $W_1$, wherein "%" indicates fetching remainder. The region of the discarded portion will not exceed $$\frac{1}{x} + \frac{1}{y}$$

of the region of the whole view plane, which accounts for a very small proportion. Furthermore, no information is included at the boundary. Therefore, such a process will not influence the imaging result.

Figure 3:
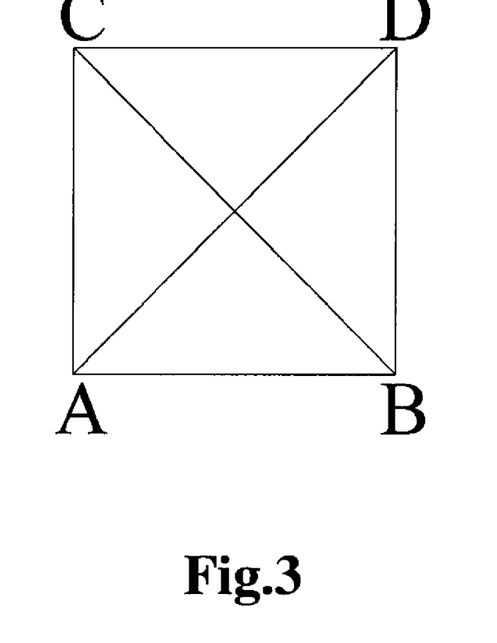
FIG. 3 is a schematic diagram of a grid, in which A, B, C and D indicate vertices respectively and an diagonal line indicates cross-comparison relation.

For each first-level grid, it is firstly to projectively calculate the gray-scale values of pixels on four vertices A, B, C and D as shown in FIG. 3 which are denoted as $I_A$, $I_B$, $I_C$ and $I_D$ (as the ray casting algorithm is a classical method, its implementation is not described in detail herein). Then, it is required to determine whether or not the four gray-scale values have smaller differences. Thus, an determining method known as "cross-comparison" is adopted herein with the formula as follows:

$$\begin{cases} |I_A - I_D| < T \\ |I_B - I_C| < T \end{cases}, \quad (2)$$

in which the formula for calculating the threshold T is:

$$T = \frac{\delta}{W_1} \cdot \frac{I_A + I_B + I_C + I_D}{4}, \quad (3)$$

wherein T is proportional to the mean value of the gray-scale values of four vertices A, B, C and D, but inversely proportional to the first-level side length $W_1$, and the coefficient δ is a constant which is equal to 2 upon experience.

If formula (2) is true, the current grid is "flat". Then, it is to be considered that the image in the current grid has no abundant details. Therefore, gray-scale values of remaining pixels in the grid can be obtained by interpolating the gray-scale values of four vertices A, B, C and D (herein not to detail the use of classical interpolation method such as a bilinear or a non-linear interpolation), thereby filling the whole grid quickly.

Figure 4:
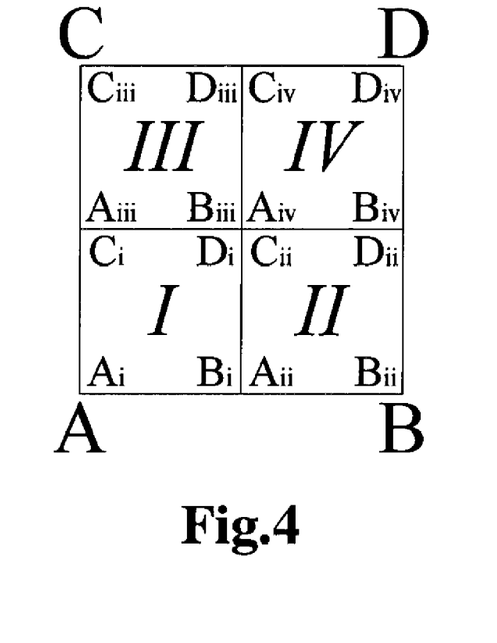
FIG. 4 is a schematic diagram of four second-level grids I, II, III and IV obtained by dividing the first-level grid shown in FIG. 3.

If formula (2) is untrue, the current grid is "non-flat". Then, the grid is subdivided evenly into four sub-grids I, II, III and IV referred to as "second-level grids" arranged in the shape of "田"(i.e. arranging in a 2×2 array), as shown in FIG. 4. The side length of the four sub-grids is $$W_2 = \frac{W_1}{2}$$

known as "second-level side length". The similar calculation and determination are performed on each second-level grid as on the first-level grid, taking Grid I as an example:

In FIG. 4 for the projective calculation, the gray-scale values of pixels on four vertices $A_i$, $B_i$, $C_i$ and $D_i$ are denoted as $I_{Ai}$, $I_{Bi}$, $I_{Ci}$ and $I_{Di}$, and the cross-comparison method is still used to determine whether or not the four gray-scale values have small differences with the formula as follows:

$$\begin{cases} |I_{Ai} - I_{Di}| < T \\ |I_{Bi} - I_{Ci}| < T \end{cases}, \quad (4)$$

in which the formula for calculating the threshold T is:

$$T = \frac{\delta}{W_2} \cdot \frac{I_{Ai} + I_{Bi} + I_{Ci} + I_{Di}}{4}. \quad (5)$$

Compared with formulae (2) and (3), formulae (4) and (5) substitute $I_{Ai}$, $I_{Bi}$, $I_{Ci}$ and $I_{Di}$ for $I_A$, $I_B$, $I_C$ and $I_D$, and $W_2$ for $W_1$, which means that the criteria for determining will be looser as the size of the grid becomes smaller.

If formula (4) is true, Grid I is "flat". Then, the gray-scale values of remaining pixels in the grid can be obtained by interpolating the gray-scale values of four vertices $A_i$, $B_i$, $C_i$ and $D_i$, thereby filling the whole grid quickly.

If formula (4) is untrue, Grid I is "non-flat". Then, the grid I is subdivided evenly into four sub-grids arranged in shape of "田"(i.e. arranging in a 2×2 array), which further generates four "third-level grids". Analogically, the similar processes of determining, interpolation filling and dividing are performed, in which the subdivision of n–1-level sub-grid will generates four n-level sub-grids with the side length of:

$$W_n = \frac{W_{n-1}}{2} = \frac{W_{n-2}}{4} = \cdots = \frac{W_1}{2^{n-1}}. \quad (6)$$

Meanwhile, $W_n$ will substitute $W_1$ of formula (3) while it is to determine whether or not the n-level grid is flat, i.e. the general form of the formula (3) is:

$$T = \frac{\delta}{W_n} \cdot \frac{I_{An} + I_{Bn} + I_{Cn} + I_{Dn}}{4} = \frac{\delta \cdot 2^{n-3} \cdot (I_{An} + I_{Bn} + I_{Cn} + I_{Dn})}{W_1}, \quad (7)$$

wherein n is the "level" of the current grid, and $I_{An}$, $I_{Bn}$, $I_{Cn}$ and $I_{Dn}$ are gray-scale values of pixels on four vertices of the current grid.

Certainly, division can not be processed infinitely. When the level $n = \log_2 W_1$, $W_n = 2$. Then, the grid of this level can not be subdivided even though it is a non-flat grid, and projective calculation of gray-scale values of remaining pixels is required. The reason is easily understood: a grid in size of 2×2 is an "atomic" grid and can not be subdivided. Therefore, the atomic grid can be defined as a grid which can not or is unnecessary to be subdivided.

According to the above-mentioned method, the gray-scale value of each pixel within the current level grid can be obtained without omissions for rendering the current level grid. When all level grids in the view plane are rendered, the whole 3D rendering process is finished.

Figure 5:
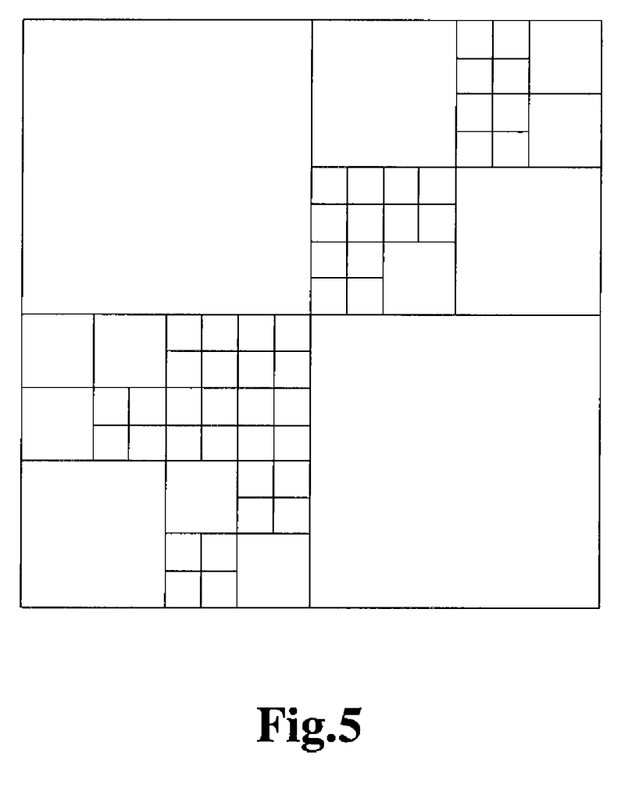
FIG. 5 is an example of dividing step by step, in which X=Y=16, x=y=2, $W_1$=16.

FIG. 5 is an example of simple division step by step, in which X=Y=16, x=y=2, $W_1$=16. That is to say, the view plane is divided into four first-level grids and the grid at maximum level is a fourth-level grid (herein referred to as only an example and such parameters will not be possible in practice).

The method for dividing step by step provided in the embodiment of the present invention can be considered as a process in which resolution of the view plane is adjusted adaptively, thereby known as a "view plane focused" algorithm. Basic principles of such an algorithm are as follows: as to the flat region (i.e. lack of details), a method of extensive interpolation is used instead of that for projecting pixel one by one, thereby time for rendering will be greatly reduced due to low projecting speed but fast interpolation; as to the non-flat region (i.e. with abundant details), as part of it might be flat, division step by step is required to quickly render the part with less details using the method of interpolation, while rendering accurately the part with more details using projecting method, thereby to realize objectives of being both quick and accurate.

Figure 6:
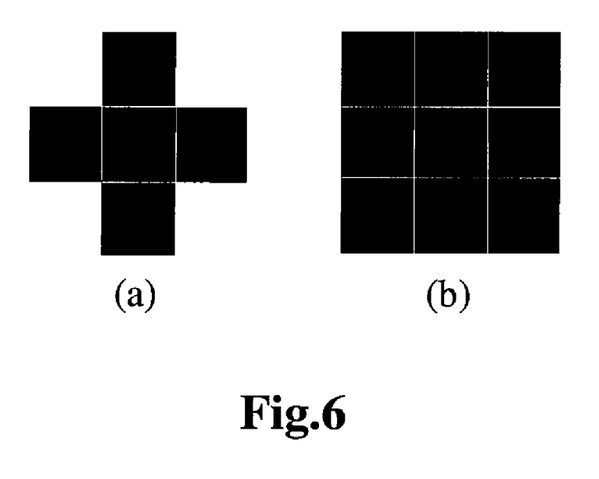
FIG. 6 shows shapes of the structural elements, in which (a) is shaped as "+"(i.e. a diamond shape) and (b) is shaped as "囲"(i.e. a square shape)

Hereinabove has introduced the basic process of the method for rendering according to the embodiment of the present invention. In fact, in order to improve robustness of this method according to the embodiment of the present invention, a morphological closing operation is required to be performed on a set of all non-flat grids generated from each determining step. Furthermore, in order to implement this operation, a breadth-first manner should be adopted in the whole flow of the method, which is described as follows:

The view plane is still divided into first-level grids. All first-level grids are determined and marked one by one as a flat or a non-flat grid, and a morphological closing operation is performed on the set of non-flat grids. It is to be noted that the units to be operated are first-level grids but not pixels. Here, a structural element shaped as "+"(i.e. a diamond shape) is adopted, as shown in FIG. 6(a), or a structural element in size of 3×3 shaped as "囲"(i.e. a square shape) or elements in other shapes may be adopted upon the requirement, as shown in FIG. 6(b). After the closing, part of flat grids will surely be remarked as non-flat grids. For current marked results, all flat grids will be fast filled with the results of interpolating the gray-scale values on four vertices, while each non-flat grid will be subdivided into four second-level grids.

As for each second-level grid of the view plane, it is required to determine and mark them one by one as a flat or a non-flat grid. As for the set of non-flat grids, a morphological closing operation is performed with taking second-level grids as units. Then, with regard to the new non-flat grids generated in closing operation, the part that occurs in initial second-level flat grids will be maintained, while the part that occurs in initial first-level flat grids will be discarded. For current marked results, all second-level flat grids will be fast filled with the results of interpolating the gray-scale values on four vertices, whereas all non-flat second-level grids will be subdivided into four third-level grids. Analogically, the processes of determining, closing operation, interpolation filling and dividing step by step are repeatedly performed till girds are subdivided into atomic grids.

In general, after all n-level grids are determined and marked, a morphological closing operation is performed on the set of n-level non-flat grids by taking the n-level grids as units. Then, as to new non-flat grids generated in closing operation, the part that occurs in initial n-level flat grids will be maintained, while the part that occurs in initial "low-level" flat grids will be discarded (no need to change the mark as low-level flat grids are surely filled through interpolation). There is provided an idea herein, i.e. if m<n, the m-level grids are low-level grids with respect to n-level grids.

Figure 7:
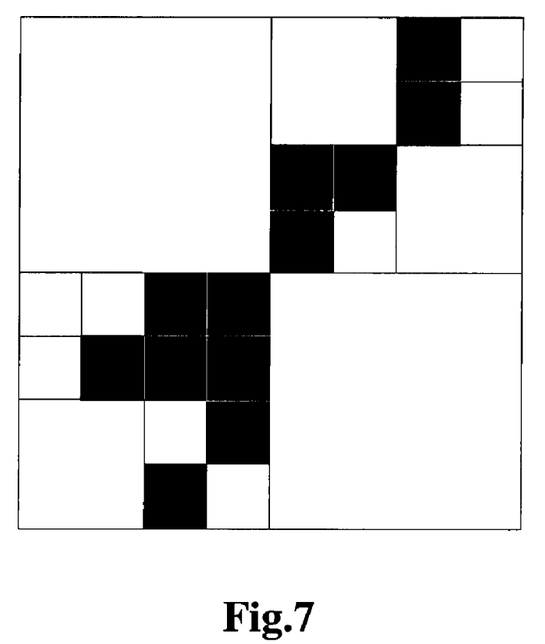
FIG. 7 shows the blackened third-level non-flat grids as shown in FIG. 5 to emphasize the unit to be performed.
Figure 8:
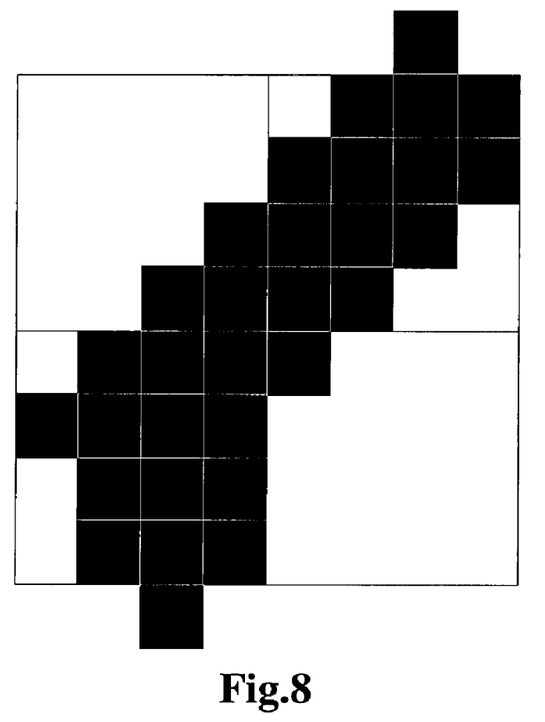
FIG. 8 is a schematic diagram of the grid in FIG. 7 after dilation operation.
Figure 9:
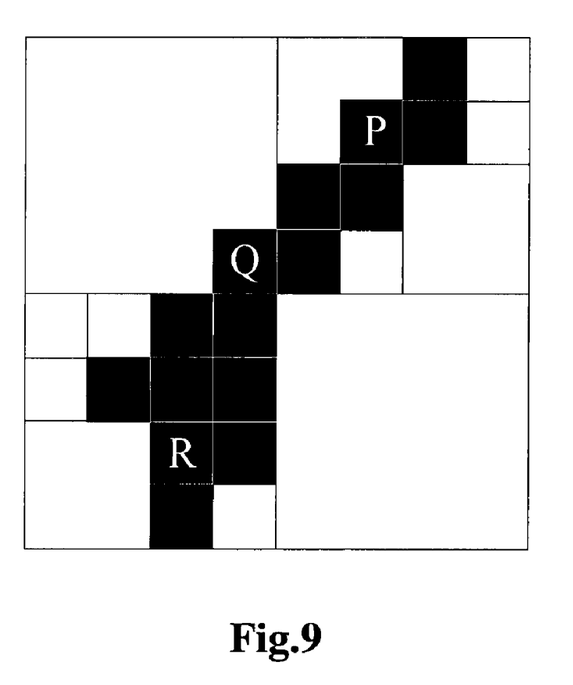
FIG. 9 is a schematic diagram of the grid in FIG. 8 after erosion, which is equivalent to the grid in FIG. 7 after closing operation.
Figure 10:
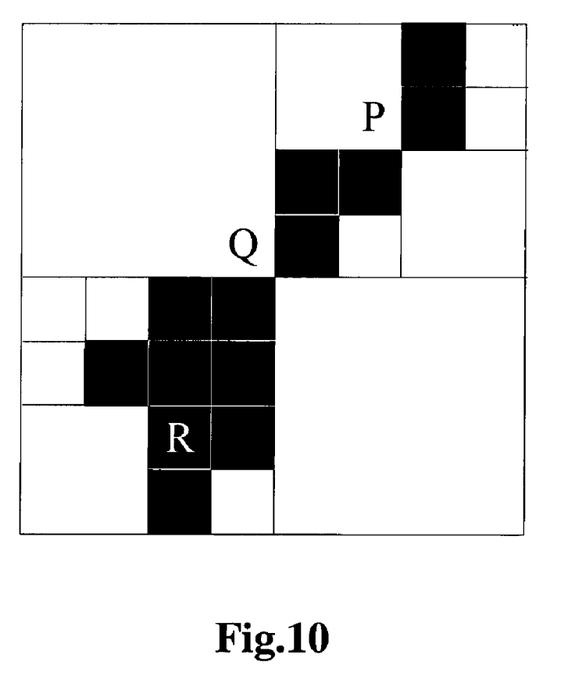
FIG. 10 is a schematic diagram of the grid in FIG. 9 after discarding the flat grids of lower level.

FIGS. 7-10 illustrate an example of the closing operation. In FIG. 5, the smallest character "囲"(i.e. a 2×2 array) represents third-level non-flat grids, wherein n=3. In FIG. 7, these grids are blackened, indicating to take third-level grids as units. FIG. 8 represents the result of performing a morphological dilation operation on the grids of FIG. 7. FIG. 9 represents the result of performing a morphological erosion operation on the grids of FIG. 8, i.e. the result of performing a morphological closing operation on the grids of FIG. 7. It is to be noted that three new units P, Q and R are added in FIG. 9 with respect to FIG. 7, in which P that occurs in initial second-level flat grids will be discarded, so will Q that occurs in initial first-level flat grids, whereas R that occurs in initial third-level flat grids will be retained. The final result is shown in FIG. 10. Obviously, only one unit R is added in FIG. 10 with regard to FIG. 7. Afterwards, subsequent steps can be carried out on and on, i.e. to fast fill white third-level flat grids by interpolating and divide the blackened third-level non-flat grids into fourth-level grids, as shown in FIG. 10.

This method of performing a morphological closing operation on the marks of the non-flat grids step by step is referred to as "non-flat region growth". The basic principles are as follows: some virtually grids abundant in details may be misdetermined as flat grids, probably because deviations among the gray-scale values on four vertices are not great; but, non-flat region growth can effectively reduce probability of the misdetermination using relationship between the adjacent grids by filling the gaps among the non-flat regions, thereby to improve the robustness of rendering according to the embodiment of the present application. Certainly, such improvement will be at the cost of slight increase in calculation amount, which is mainly represented in the increase in the projected pixels caused by dilation of the non-flat region while the calculation amount in the morphological closing operation per se can be ignored.

Figure 11:
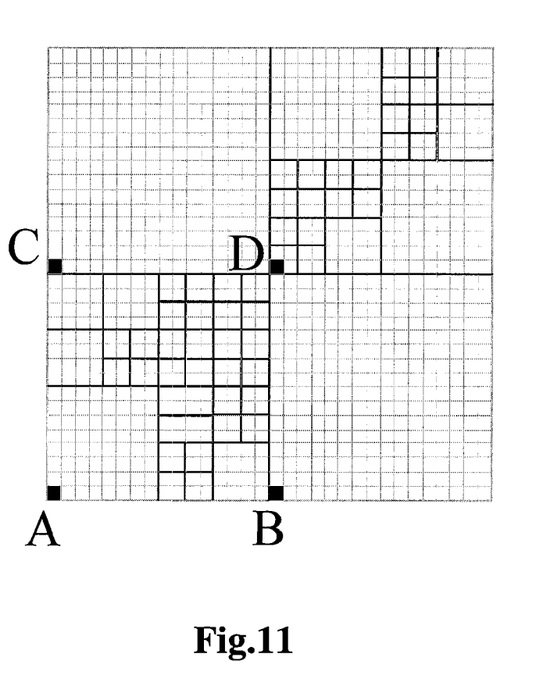
FIG. 11 is a complete form of FIG. 5, in which each small square represents a pixel and the vertices A, B, C and D of the first-level grid in the bottom left corner are blackened, and the filled region of the second-level flat grid in the bottom left corner is indicated in shadow.

In fact, relationship between adjacent grids is not only embodied in the non-flat region growth. Considering characteristics of a digital image, the vertices and the sides of adjacent grids are configured as partly overlapped. FIG. 11 is a complete form of FIG. 3, in which each small square represents a pixel. It is to be noted that vertices A, B, C and D of the first-level grid in the bottom left corner are blackened, in which Vertex B is overlapped with Vertex A on the right grid thereof, Vertex C is overlapped with Vertex A on the upper grid thereof, and Vertex D is overlapped with Vertex A on the upper right grid thereof. That is to say, the gray-scale value on only one vertex of each first-level grid is required to be calculated, while for other vertices, it is only necessary to retrieve the calculated and saved results, which is referred to as "vertex sharing". Likewise, as to n-level grids, the adjacent grids at the same level enjoy the similar vertex sharing as well. In addition, grids at different levels may also enjoy vertex sharing. For example, when the first-level grid in bottom left corner as shown in FIG. 11 is divided into four second-level grids, Vertex A of the second-level grid in bottom left corner is overlapped with Vertex A of the first-level grid.

It is to be observed that, as two adjacent grids have an overlapped boundary, they may enjoy sharing. As shown in FIG. 11, when the second-level grid in the bottom left corner is determined to be a flat grid, the entire grid can be quickly filled using the interpolated results of the gray-scale values on four vertices with the filled region shown in shadow. Then, the left side of the grid on the right and the bottom side of the upper grid are also filled synchronously, so no re-calculation is required in subsequent steps but only to retrieve the calculated and saved results, which is referred to as "boundary sharing".

Vertex sharing and side sharing are based on following: if the overlapped vertex or boundary between the current and its adjacent grids have been calculated by interpolation or projection, no recalculation is required but only to retrieve the saved results, thereby to effectively reduce the calculation amount. Furthermore, according to the rendering method of the embodiment of the present invention, the filling step by interpolating the n-level flat grids always go first, followed by the steps of dividing and calculating the n-level non-flat grids. Then, the filling results can be used in the subsequent steps, and this "interpolation-first" solution is more favorable for improving the speed with vertex sharing and boundary sharing. Thus, the 3D volume rendering method has been described thoroughly.

Figure 12:
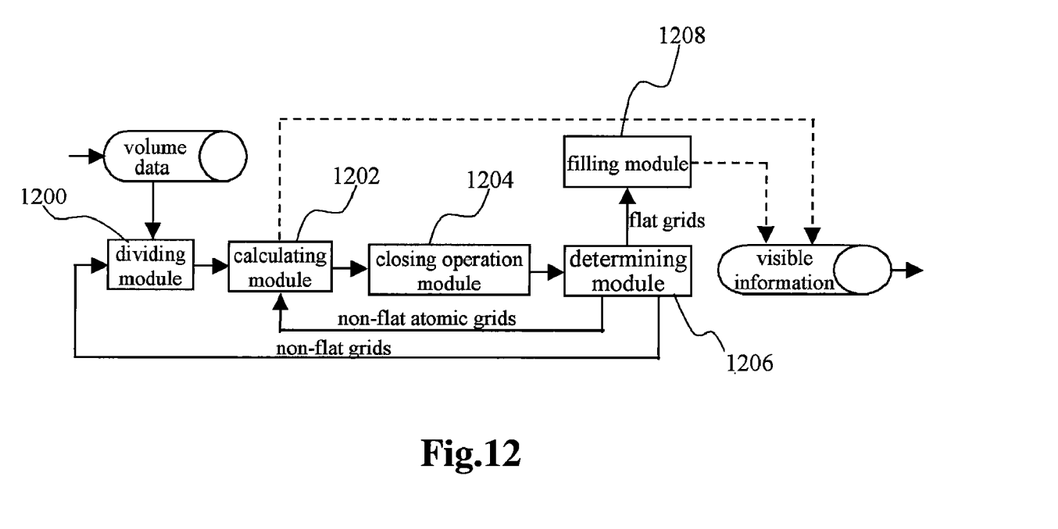
FIG. 12 is a block diagram of an apparatus for fast volume rendering of 3D ultrasound image according to the embodiment of the present invention.
Figure 13:
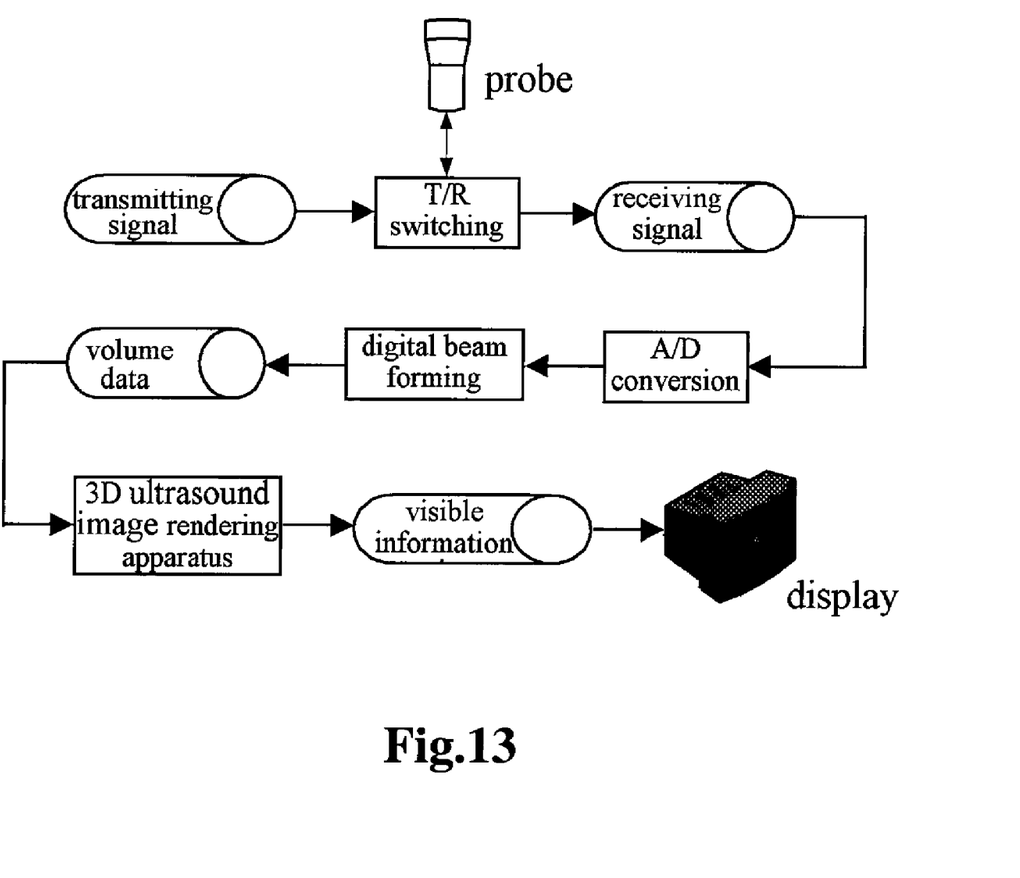
FIG. 13 is a schematic diagram of practical application of the apparatus for fast volume rendering of 3D ultrasound image according to the embodiment of the present invention.

The apparatus for fast volume rendering of 3D ultrasound image according to the embodiment of the present invention comprises a dividing module 1200, a calculating module 1202, a closing operation module 1204, a determining module 1206 and a filling module 1208, as shown in FIG. 12. Volume data is firstly processed by the dividing module 1200, in which the dividing module 1200 is used to divide a view plane into first-level grids arranged vertically and horizontally according to a predetermined size. Then, the calculating module 1202 is used to projectively calculate gray-scale values of pixels on four vertices of each grid. Next, the closing operation module 1204 is used to perform a closing operation on the non-flat grids thereof. Afterwards, the determining module 1206 is used to compare deviations of the gray-scale values of pixels on four vertices of each grid with a predetermined threshold, wherein if the deviation is smaller than the predetermined threshold, the grid is a flat grid, and if the deviation is larger than the predetermined threshold, the grid is a non-flat grid. Finally, the filling module 1208 is used to entirely fill each flat grid by obtaining gray-scale values for all pixels inside the grid through interpolating the gray-scale values of pixels on four vertices thereof. For the grid determined to be a non-flat and non-atomic grid by the determining module 1206, it returns to the dividing module 1200 to be subdivided into sub-grids and then goes through subsequent processes. For the grid determined to be a non-flat atomic grid by the determining module 1206, it returns to the calculating module 1202 for projective calculation of the gray-scale values of all pixels. Besides, the closing operation module 1204 in this structure is an optional module. FIG. 13 is a schematic diagram of practical application of the apparatus for fast volume rendering of 3D ultrasound image according to the embodiment of the present invention.

Above-mentioned embodiments have accounted for the present invention but the present invention is not limited to these embodiments. For example, the method for calculating the size of first-level grids can be changed, and side length thereof may neither be the same nor be the integer power of 2, which will influence the dividing method and the conditions for stopping division. The method for processing the edge portion of the view plane unable to be covered by the grids can be changed, i.e., said portion can be subdivided into smaller grids. The method for determining whether or not the grid is flat can be change, i.e., using other methods for measuring deviation. The method for implementing a ray casting algorithm can be changed, even though the classical method can be divided into forward composition and backward composition. The method for interpolation can also be changed, i.e., using other methods for interpolation. The method for dividing step by step can be changed, i.e. dividing can be set to stop at a certain level, or even no grid is divided, and all pixels within the non-flat grids will be calculated by means of the ray casting algorithm when stopping division. Moreover, the morphological closing operation can use the structural elements in other shapes, such as an element in size of 3×3 shaped as "⊞"(i.e. a square shape); low-level flat grids generated in the morphological closing operation can be retained; the morphological closing operation can be cancelled or replaced by a morphological dilation operation, in which the former will increase speed but decrease robustness, while the latter will decrease speed but increase robustness; the morphological closing operation can be selectively carried out, for example, to be carried out when the current level n is equal to some values but not when equal to others. Additionally, the method for vertex sharing and boundary sharing can be cancelled totally or partly, for example, to make adjacent grids have totally non-overlapped vertices and boundaries, or to only cover the boundaries in some directions when fast filling the entire grids, etc. Any modification, alternation and equivalent substitution made in the present invention should be taken within the protection scope of the present invention, only if not away from the spirit and the scope of the present invention.

The invention claimed is:

1. A method for fast volume rendering of 3D ultrasound image, comprising steps of:
dividing a view plane into first-level grids arranged vertically and horizontally according to a predetermined size;
calculating gray-scale values of pixels on four vertices of each grid by projection;
comparing deviations among the gray-scale values of pixels on four vertices of each grid with a predetermined threshold, wherein if the deviation is smaller than the predetermined threshold, the grid is determined as a flat grid, and if the deviation is larger than the predetermined threshold, the grid is determined as a non-flat grid;
filling each flat grid by obtaining gray-scale values for all pixels inside the flat grid through interpolating the gray-scale values of pixels on four vertices thereof;
wherein for the non-flat grid, the dividing step, the calculating step, the determining step and the filling step are performed repeatedly until the non-flat grid is subdivided into atomic grids so as to calculate gray-scale values for remaining pixels by projection.

2. The method according to claim 1, further comprising step of:
a morphological closing operation for performing a morphological closing operation on a set of non-flat grids in this level each time when finishing the determining step; wherein the non-flat grids generated in the closing operation which occur in the flat grids in this level are retained and which occur in low-level flat grids are discarded.

3. The method according to claim 1, wherein:
in the dividing step, adjacent grids can be divided to share vertices or boundaries.

4. The method according to claim 3, wherein:
in the calculating step, it is only to calculate the gray-scale values of pixels on non-sharing grids, and retrieve the calculated and saved results with regard to the gray-scale values of pixels on grids which share the vertices or boundaries.

5. The method according to claim 1, wherein:
in the dividing step, the view plane is divided into the first-level grids arranged vertically and horizontally according to a predetermined size that the width is equal to the height.

6. The method according to claim 5, wherein:
the width of the first-level grids is equal to its height and both are the integer power of 2, expressed as:

$$W_1 = H_1 = 2^{\lfloor log_2 min\left(\frac{X}{x}, \frac{Y}{y}\right)\rfloor}$$

in which $W_1$ and $H_1$ are the width and the height of the first-level grids respectively, X and Y are the width and the height of the view plane respectively, and x and y are numbers of columns and rows of the first-level grids respectively.

7. The method according to claim 1, wherein:
the non-flat grid is subdivided repeatedly in the dividing step into four even sub-grids shaped as "田", i.e. a 2×2 array.

8. The method according to claim 1, wherein:
in the determining step, the deviation between gray-scale values of pixels on two diagonal vertices of each grid is compared with a predetermined threshold, which is expressed as follows:

$$\begin{cases} |I_{An} - I_{Dn}| < T \\ |I_{Bn} - I_{Cn}| < T \end{cases},$$

in which the formula for calculating the threshold T is:

$$T = \frac{\delta}{W_n} \cdot \frac{I_{An} + I_{Bn} + I_{Cn} + I_{Dn}}{4} = \frac{\delta \cdot 2^{n-3} \cdot (I_{An} + I_{Bn} + I_{Cn} + I_{Dn})}{W_1},$$

wherein n is the level of the current grid, $I_{An}$, $I_{Bn}$, $I_{Cn}$, $I_{Dn}$ are the gray-scale values for four vertices of the current grid respectively, $W_n$ and $W_1$ are the width of n-level and first-level grids respectively, and a coefficient $\delta$ is a constant which is equal to 2 upon experience.

9. The method according to claim 1, wherein:
in the determining step, the variance of the gray-scale values of pixels on four vertices of each grid is compared with a predetermined threshold to determine whether or not the grid is a flat or a non-flat grid.

10. The method according to claim 1, wherein:
in the filling step, the gray-scale values for all pixels inside each grid can be obtained through a bilinear or a non-linear interpolation using the gray-scale values of pixels on four vertices of each grid.

11. The method according to claim 1, wherein:
in the dividing step, dividing can be set to stop at a certain level; and then, a ray casting algorithm is used to calculate all pixels in the non-flat grid.

12. An apparatus for fast volume rendering of 3D ultrasound image, comprising:
a dividing module for dividing a view plane into first-level grids arranged vertically and horizontally according to a predetermined size;
a calculating module for calculating gray-scale values of pixels on four vertices of each grid by projection;
a determining module for comparing deviations among the gray-scale values of pixels on four vertices of each grid with a predetermined threshold, wherein if the deviation is smaller than the predetermined threshold, the grid is a flat grid, and if the deviation is larger than the predetermined threshold, the grid is a non-flat grid; and
a filling module for entirely filling each flat grid by obtaining gray-scale values for all pixels inside the grid through interpolating the gray-scale values of pixels on four vertices thereof;
wherein the non-flat grid is processed repeatedly by the dividing module, the calculating module, the determining module and the filling module until the non-flat grid is subdivided into atomic grids so as to calculate gray-scale values for remaining pixels by projection.

13. The apparatus according to claim 12, further comprising
a morphological closing operation module for performing a morphological closing operation on a set of non-flat grids in this level each time when finishing the determining; wherein the non-flat grids generated in the closing operation which occur in the flat grids in this level are retained and which occur in low-level flat grids are discarded.

14. The apparatus according to claim 12, wherein:
the dividing module can divide the adjacent grids to share vertices or boundaries.

15. The apparatus according to claim 14, wherein:
the calculating module only calculates gray-scale values of pixels on non-shared grids, and retrieves the calculated and saved result with regard to the gray-scale values of pixels on grids which share the vertices or boundaries.

16. The apparatus according to claim 12, wherein:
the dividing module divides the view plane into the first-level grids arranged vertically and horizontally according to a predetermined size that the width is equal to the height.

17. The apparatus according to claim 16, wherein:
the width of the first-level grids is equal to its height and both are the integer power of 2, expressed as:

$$W_1 = H_1 = 2^{\lfloor log_2 min(\frac{X}{x}, \frac{Y}{y}) \rfloor}$$

in which $W_1$ and $H_1$ are the width and the height of the first-level grids respectively, X and Y are the width and the height of the view plane respectively, and x and y are numbers of columns and rows of the first-level grids respectively.

18. The apparatus according to claim 12, wherein:
the non-flat grid is subdivided repeatedly by the dividing module into four even sub-grids shaped as "田", i.e. a 2×2 array.

19. The apparatus according to claim 12, wherein:
the determining module compares the deviation between the gray-scale values of pixels on two diagonal vertices of each grid with a predetermined threshold, which is expressed as follows:

$$\begin{cases} |I_{An} - I_{Dn}| < T \\ |I_{Bn} - I_{Cn}| < T \end{cases},$$

in which the formula for calculating the threshold T is:

$$T = \frac{\delta}{W_n} \cdot \frac{I_{An} + I_{Bn} + I_{Cn} + I_{Dn}}{4} = \frac{\delta \cdot 2^{n-3} \cdot (I_{An} + I_{Bn} + I_{Cn} + I_{Dn})}{W_1},$$

wherein n is the level of the current grid, $I_{An}$, $I_{Bn}$, $I_{Cn}$, $I_{Dn}$ are the gray-scale values for four vertices of the current grid respectively, $W_n$ and $W_1$ are the width of n-level and first-level grids respectively, and a coefficient $\delta$ is a constant which is equal to 2 by experience.

20. The apparatus according to claim 12, wherein:
the determining module determines whether or not the grid is a flat or a non-flat grid by comparing the variance of the gray-scale values of pixels on four vertices of each grid with a predetermined threshold.

21. The apparatus according to claim 12, wherein:
the filling module can obtain the gray-scale values of all pixels inside each grid through a bilinear or a non-linear interpolation using the gray-scale values of pixels on four vertices of each grid.

22. The apparatus according to claim 12, wherein:
the dividing module can be set to stop at a certain level; and then, a ray casting algorithm is used to calculate all pixels in the non-flat grid.

* * * * *